United States Patent [19]

Hetrick et al.

[11] Patent Number: 5,310,474
[45] Date of Patent: May 10, 1994

[54] WORKFUNCTION BASED A/F SENSOR

[75] Inventors: Robert E. Hetrick, Dearborn Heights; Allen L. Schamp, Deaborn, both of Mich.

[73] Assignee: Ford Motor Company, Dearborn, Mich.

[21] Appl. No.: 912,389

[22] Filed: Jul. 13, 1992

[51] Int. Cl.$^5$ .............................................. G01N 27/26
[52] U.S. Cl. ..................................... 204/425; 204/426; 204/427; 324/470; 123/438
[58] Field of Search .............. 204/412, 406, 425, 426, 204/427, 153.18; 324/460, 462, 470, 464; 73/23, 32; 123/438

[56] References Cited

U.S. PATENT DOCUMENTS

| | | | |
|---|---|---|---|
| 3,416,070 | 12/1968 | McGowan, Jr. | 324/470 |
| 4,272,329 | 6/1981 | Hetrick | 204/153.18 |
| 5,028,544 | 7/1991 | Rasulev et al. | 324/470 |

OTHER PUBLICATIONS

H. Dietz, W. Haecker, and H. Jahnke, Advances in Electrochemistry and Electrochemical Engineering, vol. 10, Wiley, New York, p. 1 (1977).
E. M. Logothetis, Ceramic Engineering Science Proceedings, 8th Automotive Materials Conference, 1, 281 (1980).

Primary Examiner—John Niebling
Assistant Examiner—Bruce F. Bell
Attorney, Agent, or Firm—Peter Abolins; Roger L. May

[57] ABSTRACT

A sensor for determining the stoichiometric air to fuel ratio (A/F) at the input to the cylinders of an internal combustion engine which is based on measuring the change in the workfunction of a material which occurs when the oxidizing and reducing species in the adjacent gas phase are at or near their stoichiometric ratio. In one method the sensor includes a material which is capable of thermionically emitting alkali metal or other appropriate ions into an exhaust gas atmosphere where they are subsequently collected by a nearby collector electrode and the magnitude of the emission current is measured. The interaction of the emitting surface with the gas phase reversibly changes the workfunction of the emitting surface from large to smaller values as that gas phase is varied through the stoichiometric ratio with respect to the amounts of the oxidizing and reducing species in the gas. Such a change in workfunction of the surface is accompanied by a change in the rate of the thermionic emission at the stoichiometric ratio thereby sensing that ratio in the gas phase which is proportional to the A/F at the input to the cylinders.

7 Claims, 2 Drawing Sheets

WORKFUNCTION BASED A/F SENSOR

BACKGROUND OF THE INVENTION

1. Field of the Invention

This invention relates to an electrical means to measure the stoichiometric ratio of the concentrations of oxygen and other oxidizing gaseous species to the concentrations of various reducing gaseous species such as hydrocarbons, hydrogen and carbon monoxide as might be found in the automotive exhaust.

2. Prior Art

High temperature, solid-state, air-to-fuel ratio (A/F) sensors have seen widespread use in the automotive exhaust as the feedback control element used to maintain the A/F at the input to the cylinders of an internal combustion engine near the stoichiometric value so that any oxidizing and reducing species in the exhaust gas can most efficiently be reduced to low concentrations by an exhaust gas catalyst. The sensors actually determine the ratio of the concentrations of oxidizing and reducing species in the exhaust gas. This in turn is proportional, with a different proportionality constant for each type of fuel, to the A/F which is defined as the ratio of the mass of air to the mass of fuel that is introduced to the cylinders.

Current sensors can be conveniently divided into those which have a step-like transfer function at the stoichiometric A/F ratio (such "stoichiometry sensors" have an output which switches from low to high values as the A/F passes from oxidizing (lean) to reducing (rich) conditions at stoichiometry) and those which have a more nearly linear response over a wide range of A/F on both the rich and lean side of stoichiometry. Because the first type of device has a nonlinear transfer characteristic, it is commonly used in an oscillatory or limit-cycle feedback control strategy. The linear transfer characteristic of the latter type of device makes it advantageous for use in the proportional feedback control of A/F.

Most existing A/F sensors use either an electrochemical or a resistive principle. Thus a publication by H. Dietz, W. Haecher and H. Jahnke, in *Advances in Electrochemistry and Electrochemical Engineering,* Vol. 10, Wiley, N.Y., pg. 1 (1977), describes a solid state electrochemical cell composed, for example, of zirconium dioxide doped with yttrium dioxide, using platinum electrodes, shaped as a cylinder closed at one end with the exterior electrode exposed to the gas of interest while the interior electrode is exposed to a reference atmosphere of fixed oxygen concentration (typically air). In an automotive application this type of cell typically produces an emf between its electrodes of 20 to 30 mV under lean exhaust conditions and 800 to 900 mV under rich conditions with a step like transition occurring near stoichiometry.

Similarly, a publication by E. M. Logothetis, Ceramic Engineering Science Proceedings, 8th Automotive Materials Conference, 1, 281 (1980) describes a solid oxide (e.g. titanium dioxide) device whose resistance changes by several orders of magnitude at the stoichiometric A/F when it is alternately exposed to rich and lean exhaust gas conditions. This change in resistance is often determined using a bridge circuit in which the gas sensitive resistor in one arm of the bridge is used with a thermistor (whose temperature coefficient of resistance matches that of the A/F device but which is insensitive to the gas phase) in another appropriate arm of the bridge to compensate for any changes in resistance which occur due to temperature variations. Both of these stoichiometric A/F sensing principles can be embodied in a number of different materials. Because the electrochemical devices allow the possibility of oxygen pumping, a number of structures have used this process in combination with the measurement of the emf of the same or other cell (e.g. see U.S. Pat. No. 4,272,329 to Hetrick) in a method which enables the A/F measurement over a wide range of values.

SUMMARY OF THE INVENTION

This invention describes a device which accomplishes the stoichiometric A/F determination described above by measurement of a different physical parameter from those previously reported. In particular, this device measures the change in the workfunction of an appropriate surface as the chemical species in the gas phase adjacent to the surface, and in chemical interaction with the surface, make a corresponding change from net oxidizing to net reducing conditions.

In one embodiment, the method by which the workfunction change is measured includes monitoring the gas-induced variation in the magnitude of the thermionically emitted, alkali metal ion (e.g. Na+) current coming from a heated emitting material whose surface (the surface whose workfunction is in question) is simultaneously capable of catalyzing the chemical reaction between the oxidizing and reducing gases. The magnitude of this thermionically emitted current is an especially advantageous parameter to measure since under appropriate conditions it is exponentially sensitive to the workfunction of the emitting surface. Platinum, which is a ready host material for low concentrations of alkali metal impurities that can be thermionically emitted, is an example of a material which is simultaneously an appropriate catalytic material.

In the case of some materials the workfunction can change substantially (e.g. 1.0 V) due to the adsorption of gas phase species (e.g. oxygen). Further, when the material is exposed to a mixture of gases which will react catalytically through an adsorption mechanism, the workfunction may change significantly at the stoichiometric ratio of these reacting gases thus effecting a significant change in the thermionic current which thus serves to sense that ratio. Again Pt is a material where the above mentioned processes of catalysis, adsorption and thermionic emission are applicable.

The sensing device includes a heated, catalytic material containing alkali metal (or other impurities suitable for the thermionic emission process) and held at a positive potential relative to a nearby collector electrode. Using appropriate electrical means, the thermionic current between the emitting and collecting electrodes is measured. As the result of varying conditions, the ratio of the concentrations of oxidizing and reducing species in the gas phase adjacent to the emitting surface is caused to vary about the stoichiometric ratio for these gases. Because the gases are catalytically reacting on the emitting surface by means of an adsorption mechanism, the work function of the surface is changing at the stoichiometric ratio resulting in a large, reversible change in the thermionic current which can thus be used to sense this ratio. The emitted impurity ions may also be held in a ceramic or other appropriate reservoir in contact with the emitter and supplying material for ionic emission to the emitter by diffusion.

DETAILED DESCRIPTION OF THE INVENTION

Alkali metals such as Li, Na, K, and Cs are common impurities in many ceramic and metal materials. When these solids are heated, the volatile alkalis are thermally evaporated at modest temperatures. Thus, the alkalis have a low ionization potential (the ionization potential, IP, is proportional to the energy to remove the outermost, or least tightly bound, electron from an atom). Whether the thermal emission will occur as a neutral species (the thermal evaporation of atoms) or as charged species (the thermionic emission of positively charged ions) depends on the workfunction of the host solid. If the workfunction is large with respect to the IP of the atoms, it is energetically easy for the atom to leave its outermost electron on the metal and be thermionically emitted. Thus Cs with an IP of 3.9 V is often thermionically emitted while Li with an IP of 5.8 V is most often thermally evaporated as an atom. Pt with a workfunction of about 5.0 V is a good host material for the thermionic emission of the alkali metals.

Figure 1:
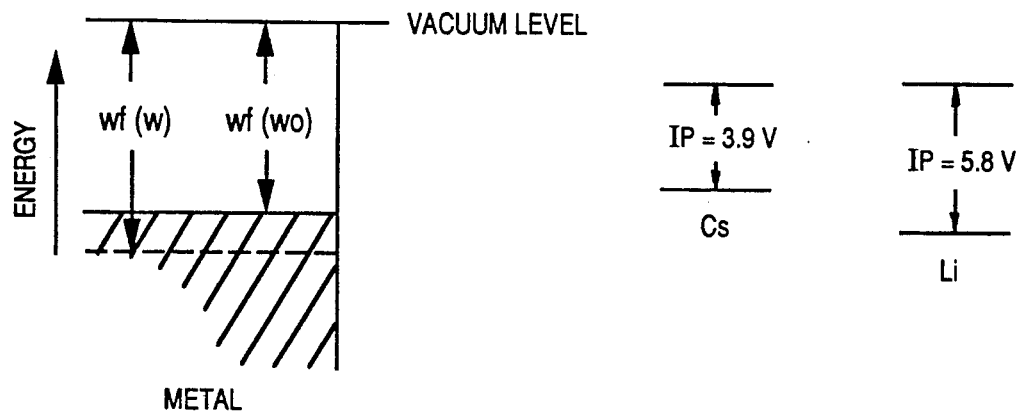
FIG. 1 is a schematic diagram showing the workfunction, wf, of the emitting surface with, wf(w), and without, wf(wo), an oxide layer as well as the ionization potential, IP (these values are appropriate for alkali atoms in the gas phase and may be modified somewhat as the alkali atoms approach a surface) of two alkali metal atoms which may be adsorbed on the surface and thus thermionically emitted if the temperature is raised.

These ideas are illustrated schematically in FIG. 1 which shows the solid workfunction with, wf(w), and without wf(wo), an oxide layer. This parameter is proportional to the energy required to remove the most energetic electron that is bound in the solid to the vacuum energy level where it could leave the solid if drawn away with an electric field for example. The energy scale is vertical in the drawing. IP is the comparable parameter for atoms or molecules and the values for two alkali metals (which have low values of IP) are shown.

Electrons may transfer between atoms or molecules hitting the surface and the solid. Electrons would move from the species with the lowest binding energy to that with the greatest binding energy. As will be discussed further below, when the solid is exposed to an oxidizing gaseous ambient, the oxidizing species can interact with the surface and modify the workfunction (e.g. to a new value, wf(w), assuming that oxygen is the oxidizing species) thereby changing the rate of the thermionic emission. For electrons a high emission rate is promoted by a low workfunction; however, for positive ion emission as in the present case, the situation is more complicated and usually a high workfunction promotes stronger emission since it becomes easier for the surface impurity species (the alkali atom) to leave its outermost electron in the solid and thermionically emit as an ion rather than thermally evaporate as an atom. Solid state ion emitters based on this method are attractive since one avoids the complexity and cost of generating a gaseous plasma as an ion source.

Figure 2:
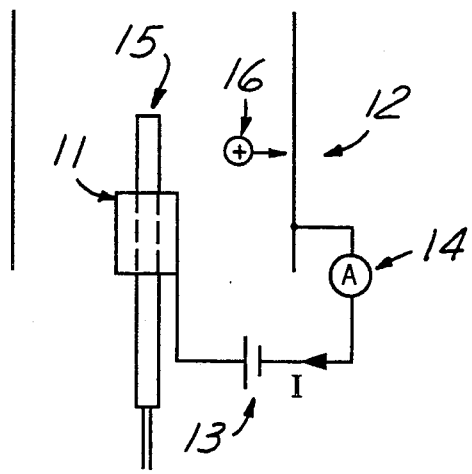
FIG. 2 is a schematic diagram of an emitting configuration in which a thin Pt sheet containing the impurities to be emitted is wrapped around a ceramic heater and held at a fixed distance and at a fixed positive potential from a collector electrode.

FIG. 2 shows the schematic diagram of a device in which a thin Pt emitter film 11 is tightly wrapped around a pencil-like ceramic heater 15 which has a region (that surrounded by the Pt) that can attain temperatures of 800° C. or higher. This emitter electrode is surrounded by a steel collector electrode 12 held at a distance of a few millimeters from the emitter. A battery 13 connected between the two electrodes holds the emitter at a positive potential ($V_{EC}$) with respect to the collector while an ammeter 14 measures the magnitude of the thermionic current I (typically in the nA regime). Mass spectrographic studies indicated that ions 16 emitted from the heated (to greater than 400° C. to achieve nA current levels) Pt where those of Na and K. When the emitting Pt is in the form of a sputtered film or a conducting metal-ceramic composite deposited on the heater, larger emitter currents can be obtained when the ceramic is doped with the alkali. The ceramic presumably supplied these atoms to the metal surfaces for thermionic emission by diffusion.

Figure 3A:
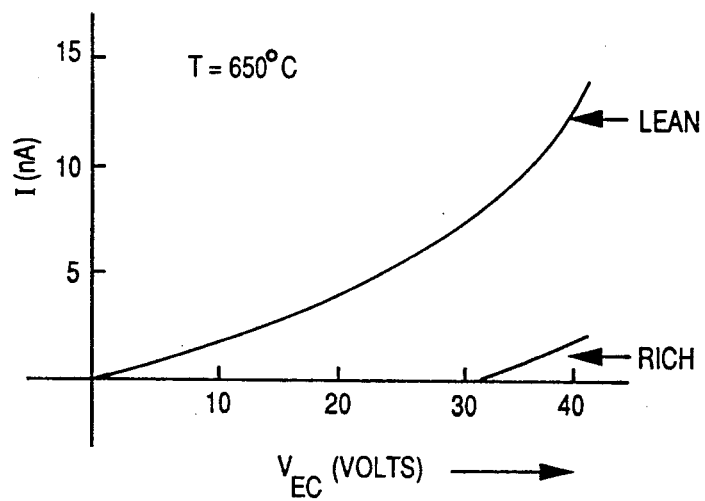
FIG. 3a is a graphical representation of the thermionic current I as a function of the emitter to collector voltage ($V_{EC}$) for rich and lean ambient gas conditions.

FIG. 3a shows a typical plot of thermionic current versus emitter to collector voltage. When the emitter is negative relative to the collector, the current flow is very low (in the subpicoampere regime) while that with the opposite emitter bias shows a greater than linear increase in the nA regime. The values shown are typical for an operating temperature of 650° C. with these devices. In summary, the current-voltage characteristic is that of a thermionic diode in which the emitted carriers are of a positive sign and the conducting medium into which the ions are emitted is relatively resistive. In this case the resistance is provided by the collision of the positive ions with the neutral ambient gas phase (e.g. air) molecules which results in an ion mobility in the vicinity of 3 cm$^2$/volt-sec at 100 kPa. Numerous results confirm this basic model.

For example, if the I vs $V_{EC}$ characteristic is measured at reduced ambient pressure, the conductivity at positive emitter biases increases inversely with the pressure until a maximum current flow is encountered in the range of 0.01 kPa. This inverse dependence is consistent with the ion scattering mechanism mentioned above. At reduced pressure, the ion emission shows a saturation with increasingly positive emitter bias. Further, this saturation current (as w .h the thermionic current in all circumstances) increases with temperature in a manner consistent with thermionic emission.

FIG. 3a also shows that the exposure of the emitting surface to a rich ambient causes a large reduction (as large as a factor of 100 depending on the temperature) in the emission at all emitter-collector voltages. The change from large to small currents occurs at the stoichiometric ratio of the oxidizing and reducing gases in the ambient.

Figure 3B:
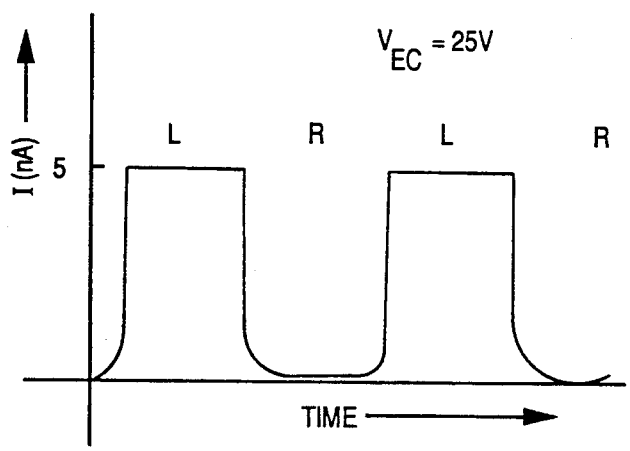
FIG. 3b is a graphical representation of the variation in I with time as the ambient is alternately switched between rich (R) and lean (L) conditions.

FIG. 3b shows a graphical representation of the alternating change in the emission current from high to low values as the A/F ratio is changed from lean (L) to rich (R) conditions respectively. Tests were run with a carrier gas of nitrogen (approximately 99%) with propane and oxygen (oxygen is at a 5:1 partial pressure excess over propane at stoichiometry) as the reducing and lean species. This effect is the basis of using the device as a stoichiometric A/F sensor. The changes shown in FIG. 3b are for changes in A/F in the immediate neighborhood of stoichiometry as would occur in a typical automotive combustion application where large departures from stoichiometry are usually not desirable. The emission is not constant for all lean or rich A/F but the changes are small, except for those occurring at stoichiometry, when the reactive gases are a small fraction (e.g. <1%) of the total ambient concentration.

Figure 4:
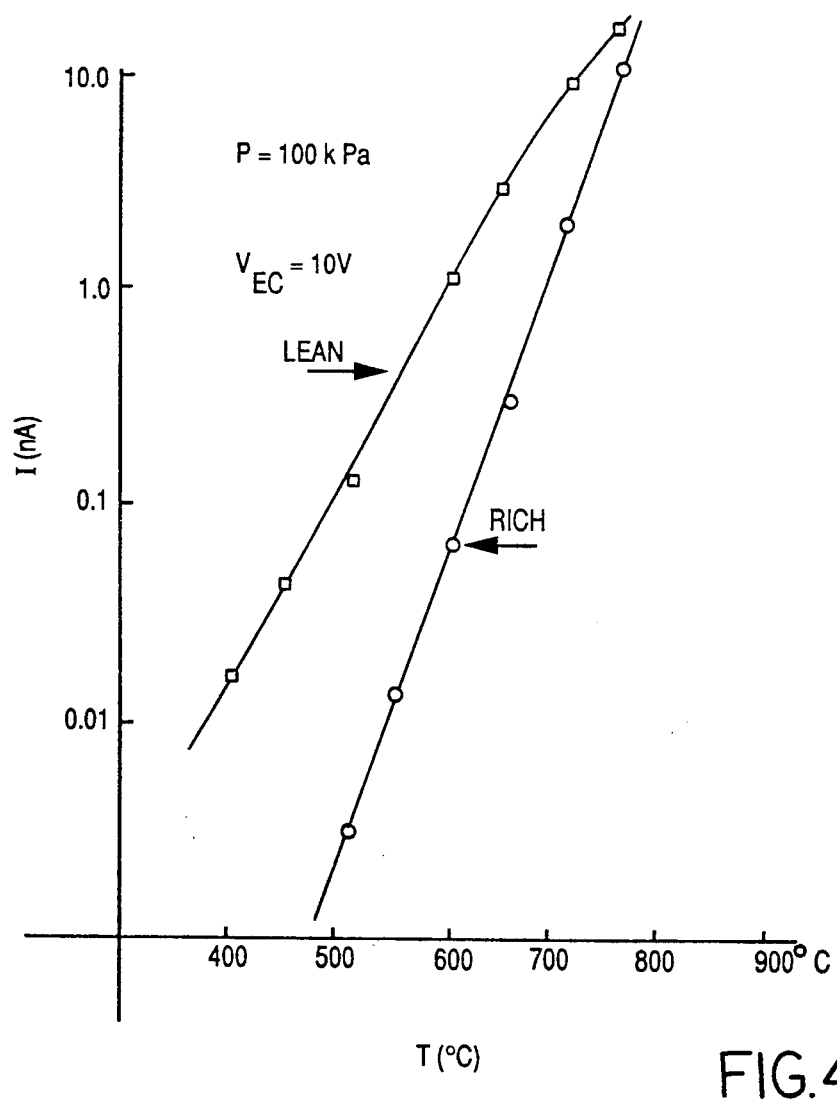
FIG. 4 is a graphical representation of a plot of both a rich (using propane as the reducing gas) and a lean (using oxygen as the oxidizing gas) ambient on I as a function of temperature at 100 kPa for a given $V_{EC}$.

FIG. 4 shows the temperature dependence of the rich and lean emission current at one atmosphere pressure (100 kPa) and $V_{EC}=10$ V. This semilog plot shows that the ratio between lean and rich currents, which can be as high as 100 at the low temperature of 450° C., becomes smaller as temperature increases with the two values eventually merging around 850° C. This plot indicates that the emission process is thermally activated and that the activation energy is lower under lean ambient conditions. This result is reasonable in the likely possibility that that activation energy for thermionic emission is in part determined by the workfunction of the Pt in a manner such that a larger workfunction (which makes it energetically easier for an adsorbed alkali atom to transfer its electron to the Pt) corresponds to a smaller activation energy. It is well known that lean or oxidizing ambient conditions can increase the workfunction of many metals by as much a 1 V. This can arise when adsorbed oxygen attracts metal electrons leading to a surface double layer which is of the right sign to increase the workfunction.

If on passing to a rich ambient, reducing species react with and remove the adsorbed oxygen, then a corresponding reduction of the workfunction is indicated with a corresponding increase in the activation energy (and decrease in current) for the thermionic emission of adsorbed alkalis. In summary, it appears that the A/F ratio sensing phenomena of this work is one in which the gas phase modulates the workfunction of an appropriate material and accordingly the rate of thermionic emission of alkali dopants in the structure is also modulated.

Various modifications and variations will no doubt occur to those skilled in the various arts to which this invention pertains. For example, the geometric configuration of the sensor structure need not be cylindrical but might advantageously have a planar geometry. These and all other variations which basically rely on the teachings through which this disclosure has advanced the state of the art are properly considered within the scope of this invention.

What is claimed is:

1. An electrical sensing structure, having a surface material, for sensing a stoichiometric ratio of an oxidizing and a reducing species in an ambient gas phase, the surface material having a work function which undergoes a reversible change in magnitude as the ratio of the concentrations of the oxidizing and reducing species passes through its stoichiometric value as a result of the interaction of these species with the surface material, and a means for measuring a reversible change by electrically monitoring the change in the workfunction so that the value of the ratio, to the extent that it is either above or below the stoichiometric value, can be known.

2. An electrical sensing structure as recited in claim 1 in which said surface material is chosen from a group including platinum and a platinum-ceramic composite.

3. An electrical sensing structure as recited in claim 1 for sensing the stoichiometric ratio of an oxidizing and reducing species in an ambient gas phase wherein said surface material includes:

a thermionically emitting surface and supporting structure including a catalyst for promoting a reaction between the oxidizing and reducing species;

said emitting surface being such that when the amount of the oxidizing species exceeds the stoichiometric ratio with respect to the reducing species in the gas phase, the oxidizing species is adsorbed from the gas phase onto said surface in a manner such that a workfunction of said surface is increased as a result of the adsorption;

said emitting surface also being such that when the amount of the reducing species exceeds the stoichiometric ratio with respect to the oxidizing species in the gas phase, the reducing species will react with and remove oxidizing species adsorbed on said emitting surface thereby reducing the workfunction of that surface;

said emitting surface and supporting structure containing a dopant for the thermionic emission of said dopant as a positive ion from that surface into the surrounding ambient;

an emitter electrode including surface supporting structure and said dopant, and being one in which the rate of thermionic emission of the dopant reversibly increases/decreases with an increase/decrease in the workfunction of said emitting surface;

a collector electrode electrically insulated from said emitter electrode and placed so that it can electrically collect the ions emitted from said emitter electrode;

said collector electrode being spaced from said emitter electrode and so designed so that the ambient gas phase to be sensed can establish itself within a space between said collector and emitter electrodes and be exposed to said emitter electrode;

a first circuit means coupled to said emitter and collector electrodes to provide a potential difference between said emitter and collector electrodes such that said emitter electrode is at a higher positive potential than said collector electrode and including a current sensing means which has an electrical output proportional to the magnitude of the measured thermionic current; and a heating element adjacent to said emitter electrode for raising said emitter electrode temperature to a high enough value to allow thermionic emission.

4. An electrical sensing structure as recited in claim 3 wherein material for said emitter and collector electrodes is chosen from a group including platinum and platinum-ceramic composites.

5. An electrical sensing structure as recited in claim 3 wherein said heating element is in contact with said emitting electrode and includes a ceramic encapsulation.

6. An electrical sensing structure having a surface material, for sensing a stoichiometric ratio of an oxidizing and a reducing species in an ambient gas phase including means for measuring a reversible change that occurs at this stoichiometric ratio in a workfunction of said surface material which are alternately exposed to, and interact with, the oxidizing and reducing gaseous species; and wherein said surface material includes:
- a thermionically emitting surface and supporting structure including a catalyst for promoting a reaction between the oxidizing and reducing species;
- said emitting surface being such that when the amount of the oxidizing species exceeds the stoichiometric ratio with respect to the reducing species in the gas phase, the oxidizing species is absorbed from the gas phase onto said surface in a manner such that a workfunction of said surface is increased as a result of the adsorption;
- said emitting surface also being such that when the amount of the reducing species exceeds the stoichiometric ratio with respect to the oxidizing species in the gas phase, the reducing species will react with and remove oxidizing species adsorbed on said emitting surface thereby reducing the workfunction of that surface.
- said emitting surface and supporting structure containing a dopant for the thermionic emission of said dopant as a positive ion from that surface into the surrounding ambient;
- an emitter electrode including said emitting surface supporting structure and said dopant, and being one in which the rate of thermionic emission of the dopant reversibly increases/decreases with an increase/decrease in the workfunction of said emitting surface;
- a collector electrode electrically insulated from said emitter electrode and placed so that it can electrically collect the ions emitted from said emitter electrode;
- said collector electrode being spaced from said emitter electrode and so designed so that the ambient gas phase to the sensed can establish itself within a space between said collector and emitter electrodes and be exposed to said emitter electrode;
- a first circuit means coupled to said emitter and collector electrodes to provide a potential difference between said emitter and collector electrodes such that said emitter electrode is at a higher positive potential than said collector electrode and including a current sensing means which has an electrical output proportional to the magnitude of the measured thermionic current; and
- a heating element adjacent to said emitter electrode for raising said emitter electrode temperature to a high enough value to allow thermionic emission; and
wherein said dopant is an alkali metal.

7. An electrical sensing structure for sensing the stoichiometric ratio of an oxidizing and a reducing species in an ambient gas phase including:
- a thermionically emitting surface and supporting structure including a catalyst for promoting a reaction between the oxidizing and reducing species;
- said emitting surface being such that when the oxidizing species exceeds a stoichiometric amount with respect to the reducing species in the gas phase, the oxidizing species is adsorbed from the gas phase onto said surface in a manner such that a workfunction of said surface is increased as a result of the adsorption;
- said emitting surface also being such that when the reducing species exceeds a stoichiometric amount with respect to the oxidizing species in the gas phase, the reducing species will react with and remove oxidizing species adsorbed on said surface thereby reducing the workfunction of said surface;
- said emitting surface and supporting structure containing an alkali metal dopant for the thermionic emission of said dopant as a positive ion from said surface into the surrounding ambient;
- an emitter electrode of a platinum material including said emitting surface supporting structure and said dopant and being one in which the rate of thermionic emission of said dopant reversibly increases/decreases with an increase/decrease in the workfunction of said emitting surface;
- a collector electrode electrically insulated from said emitter electrode and placed so that it can electrically collect the ions emitted from said emitter electrode;
- said collector electrode being spaced from said emitter electrode and so designed so that the ambient gas phase to be sensed can establish itself within a space between said collector and emitter electrodes and be exposed to said emitter electrode;
- a first circuit means coupled to said emitter and collector electrodes to provide a potential difference between said emitter and collector electrodes such that said emitter electrode is at a higher positive potential than said collector electrode and including a current sensing means which has an electrical output proportional to the magnitude of the measured thermionic current; and
- a ceramic encapsulated heating element adjacent said emitter electrode for raising the temperature of said emitter electrode to a high enough value to allow thermionic emission.

* * * * *